June 24, 1958 H. M. TIRET Plant Pat. 1,719
FUCHSIA
Filed Oct. 25, 1957
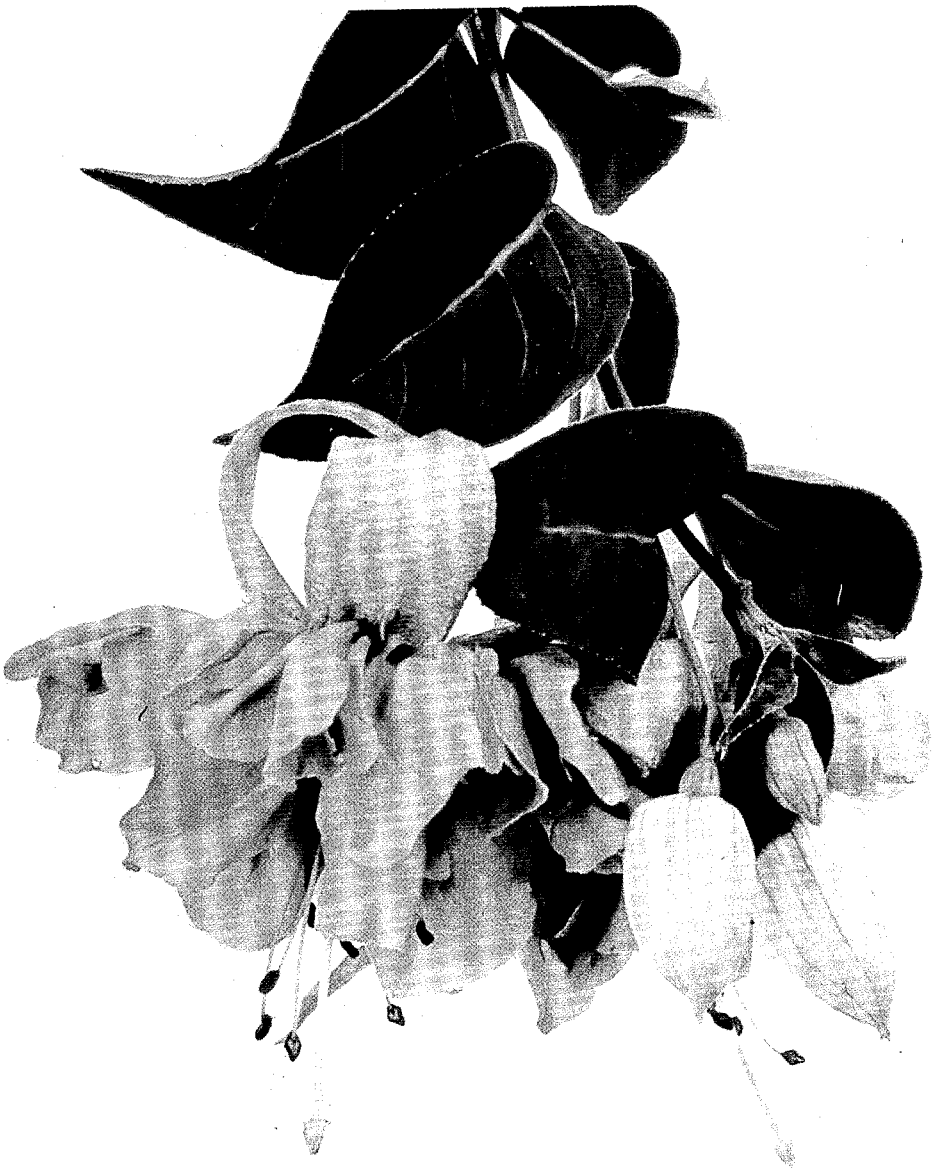

United States Patent Office

Plant Pat. 1,719
Patented June 24, 1958

1,719

FUCHSIA

Horace M. Tiret, San Francisco, Calif.

Application October 25, 1957, Serial No. 692,510

1 Claim. (Cl. 47—60)

This invention relates to a new and improved fuchsia plant, the principal new and different characteristic of which is the color and flowering habits of the plant combining pale blue flowers with contrasting crimson sepals in a flaring form of corolla.

As a hybrid from Innocence (unpatented) and 3–36–5 (unpatented), the figures representing the applicant's own breeding symbols. The plant has been asexually reproduced at Colma, California, and Gardena, California, by cuttings which retained the characteristics of the parent fuchsia.

The plant is a vigorous, upright grower. The very large flowers grow in clusters throughout the foliage, and large quantities of blooms are produced. All of the petals hyacinth Blue (British Horticultural Color Chart #40/2) in the early stage of the flowers' development. When fully developed, the petals are Amethyst Violet (British Horticultural Color Chart #35/3 and 35/2).

In the accompanying drawing, the figure shows a typical branched tip, the drawing representing approximate actual size.

A detailed description of this new variety of fuchsia plant follows:

*Habit of growth.*—This is an upright variety, quite vigorous, and medium early, heavy bloomer.

*Foliage.*—The leaves are large, dark green in color, deeply veined, grow in profusion. In appearance the leaves are crinkly. The branches are green with red shadings. The mature leaf is approximately 3¼″ in length, and 2⅛″ in width at the widest point. The edges are slightly serrated. The under side of the leaf is lighter green in color than the top side.

*Buds.*—These are pale carmine veined with deep carmine as the buds mature, with light green tips. The buds are large in size and lantern shaped. The length from the ovary is approximately 2″, and the width at the widest point is approximately 1¾″.

*Ovary.*—Light bright green in color. Length approximately ½″, and width at widest point approximately ¼″, when the flower is fully opened.

*Sepals.*—Four in number, 2⅛″ in length, and 1 1/16″ in width at the widest point. The form of the sepal is broad and irregularly curved when the flower is fully matured. The under side has a definite crepe-like appearance, while the outer side is smooth and satiny.

*Tube.*—Short and medium slender. Length is approximately ½″ and the width at the widest point is approximately 5/16″.

*Stamens.*—Eight in number, colored burgundy with same colored anthers. Length, approximately 1¾″.

*Pistil.*—The style is approximately 3″ in length measured from the tip of the ovary. It is approximately 1/32″ in width, colored pale carmine. The stigma is creamy white.

*Petals.*—The petals number approximately 28. They are exceptionally large, with a flaring corolla. The diameter of the open, mature flower is approximately 3¼″. Length of the large petals is approximately 1¾″, and the width approximately 1 5/16″ fully spread out. The petals are smooth and velvety in appearance, and are colored Hyacinth Blue (British Horticultural Color Chart #40/2) in the early stage of the flower's development, and colored Amethyst Violet (British Horticultural Color Chart #35/3 and 35/2) at maturity. The veining at the base is Crimson (British Horticultural Color Chart #22/2).

*Color of sepals and tube.*—The under side of the sepals is Crimson (British Horticultural Color Chart #22/3) darkening as the flower matures to Crimson (British Horticultural Color Chart #22/1). The top side of the sepal is Crimson (British Horticultural Color Chart #22/3) flushed with Crimson (British Horticultural Color Chart #22/2). The tube is Crimson (British Horticultural Color Chart #22/3) when the flower first opens, and as the flower matures the tube shades to Crimson (British Horticultural Color Chart #22/1).

*Parentage.*—Innocence (unpatented), and 3/36/5 (unpatented) applicant's own breeding symbols.

Having thus disclosed my discovery I claim:

A new and distinct variety of fuchsia plant herein described and illustrated, characterized by its flaring formed pale blue colored corolla, combined with contrasting crimson sepals.

No references cited.